(12) United States Patent
Webb

(10) Patent No.: US 6,360,479 B1
(45) Date of Patent: Mar. 26, 2002

(54) METHOD FOR DEFLOWERING SWEET GUM TREES TO ELIMINATE SEED AND FRUIT DEBRIS

(76) Inventor: Roger S. Webb, 11406 SW. 16th St., Micanopy, FL (US) 32667

( * ) Notice: Subject to any disclaimer, the term of this patent is extended or adjusted under 35 U.S.C. 154(b) by 0 days.

(21) Appl. No.: 09/493,913

(22) Filed: Jan. 28, 2000

Related U.S. Application Data

(60) Provisional application No. 60/144,263, filed on Jul. 15, 1999.

(51) Int. Cl.[7] .................................................. A01H 3/04
(52) U.S. Cl. ........................................... 47/57.5; 47/58
(58) Field of Search ..................................... 47/57.5, 58

(56) References Cited

U.S. PATENT DOCUMENTS 4,144,673 A * 3/1979 Quast et al. .................. 47/57.5

OTHER PUBLICATIONS

Sexton, Roy and Roberts, Jeremy A.; Cell Biology of Abscission, 1982 Annual Review of Plant Physiology, vol. 33, pp. 133–162.

Davies, Mauseth, Raven, Salibury and Ross, 1995, www-.bio.metu.tr/~e068741/project/auxin.html, p. 3, 4.*

Clarke, http://users.lycaeum.org/~sunny/botany2.htm, p. 8.*

* cited by examiner

Primary Examiner—Peter M. Poon
Assistant Examiner—Floris C Copier
(74) Attorney, Agent, or Firm—Simpson, Simpson & Snyder, PLLC

(57) ABSTRACT

A method of deflowering a sweet gum tree by injecting a solution containing indolebutyric acid into vascular tissue of the tree is disclosed for preventing undesirable seed and fruit debris.

6 Claims, 1 Drawing Sheet

METHOD FOR DEFLOWERING SWEET GUM TREES TO ELIMINATE SEED AND FRUIT DEBRIS

This Appln claims benefit of Prov. No. 60/144,263 filed Jul. 15, 1999.

BACKGROUND OF THE INVENTION

A. Field of the Invention

The present invention relates generally to the field of arboriculture, and more particularly to a method of eliminating unwanted seed and fruit debris from sweet gum trees.

B. Description of the Prior Art

The genus Liquidambar belongs to the Witch-hazel family (Hamamelidaceae) and, along with two other genera, comprises the principal timber-contributing members of the twenty-three genera in this family. Among these is *L. styraciflua*, or sweet gum tree. The sweet gum tree is an important hardwood in the southern United States both for its commercial use as a low-quality wood and fiber source and for its use as a preferred ornamental species for southern landscape enhancement. Because of its ability to produce large annual quantities of seed from many fruiting heads per tree, sweet gum also presents a nuisance in ornamental settings due to its seed and fruit head debris. The flowers of sweet gum are unisexual and the tree species is monoecious, whereby male and female flowers are produced separately on the same tree. Both male and female flowers are produced in heads, with the greenish-yellow staminate (male) heads borne in tight-rounded clusters (racemes) on a stiff spike. Pistillate heads are pale green, consisting of two-beaked pistils subtended by small scales borne in large numbers at the ends of drooping or angling terminal stalks. Annual fruiting clusters mature into semi-woody, pendent balls or fruit heads that are about 3.75 centimeters in diameter. After seed discharge, these fruit heads may persist on the tree for another year or more.

Manual flower removal has proven impractical and ineffective as a method of combating seed and fruit debris from sweet gum trees.

SUMMARY OF THE INVENTION

It is therefore an object of the present invention to reduce the likelihood of successful fertilization by interrupting the normal process of male and female flower maturation, male pollen production, and female flower fertilization to prevent the ultimate formation of fruit heads and seed.

It is another object of the present invention to obviate the need for manually deflowering sweet gum trees by providing a method for chemically deflowering sweet gum trees.

It is a further object of the present invention to provide a method of chemically deflowering sweet gum trees using micro- or macro-injection techniques.

The method of deflowering a sweet gum tree according to the present invention comprises the step of injecting a dilute solution containing indolebutyric acid, a compound historically used to promote the growth of new roots on cuttings, into the vascular tissue of a sweet gum tree. In a currently preferred method, five milliliters of a solution containing forty parts per million of indolebutyric acid in distilled water is injected through each of a plurality of pre-bored injection holes spaced every six inches about the circumference of the trunk of the sweet gum tree. The method causes delayed shedding of staminate flowers and early abortion or suppression of pistillate flowers, thereby preventing the development of fruit heads and production of seed.

BRIEF DESCRIPTION OF THE DRAWING

The nature and mode of operation of the present invention will now be more fully described in the following detailed description of a preferred embodiment taken with the accompanying drawing figure, in which.

DETAILED DESCRIPTION OF THE PREFERRED EMBODIMENT

Figure 1:
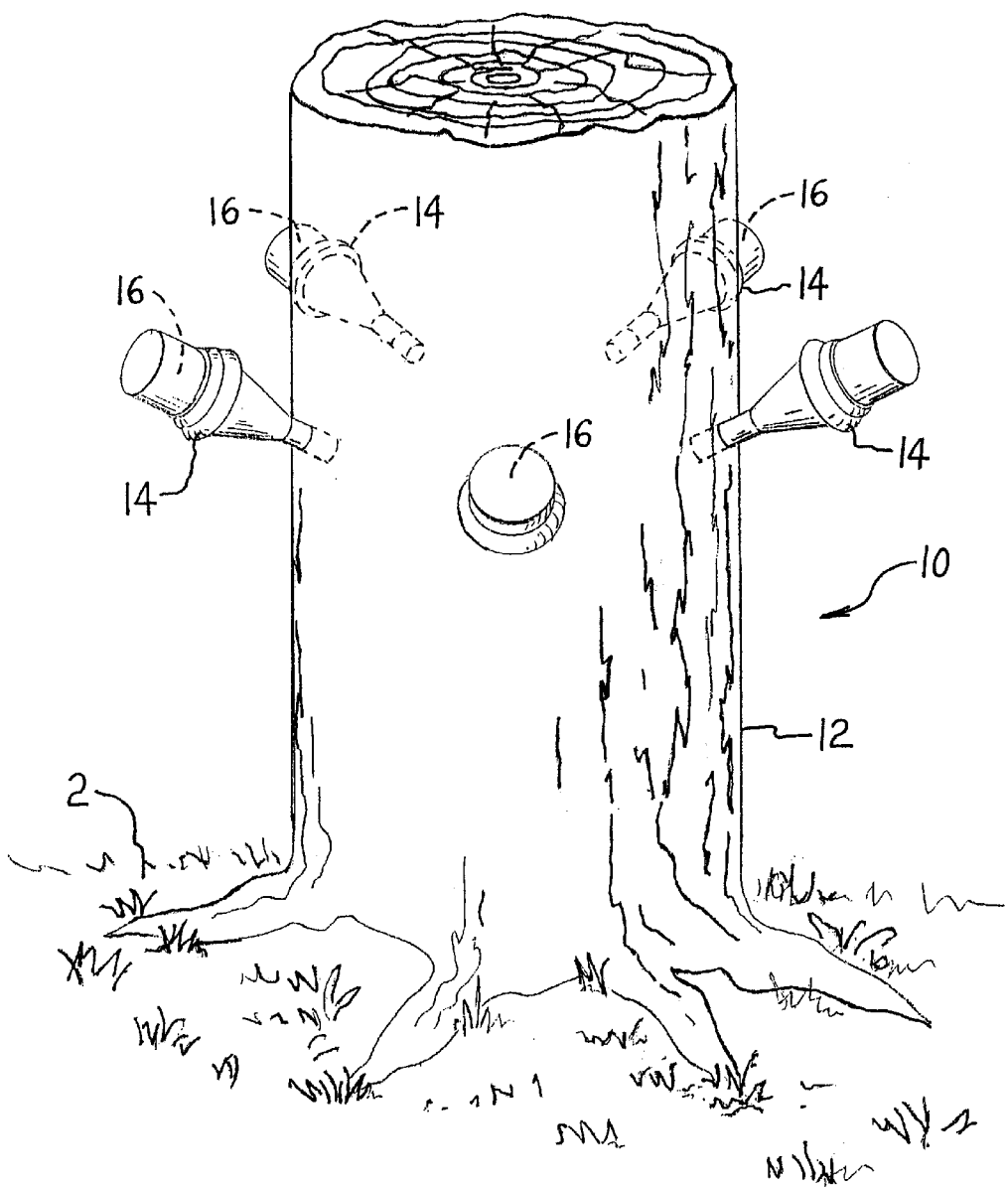
FIG. 1 is a perspective view illustrating the method of deflowering a sweet gum tree in accordance with a preferred embodiment of the present invention.

FIG. 1 illustrates the method of the present invention. The reference numeral 10 generally indicates a sweet gum tree to be deflowered, and the reference numeral 12 specifically indicates the trunk of sweet gum tree 10 growing out of ground 2. A plurality of injection units 14 are positioned at regular intervals about the circumference of trunk 12, with a discharge tube of each injection unit being inserted within a pre-formed injection hole bored or drilled at an angle through a bark layer of trunk 12 to communicate with vascular tissue of sweet gum tree 10. Injection units 14 are preferably micro-injection units designed for use with injection holes that are less than ⅜ of an inch in diameter. A suitable micro-injection unit for practicing the method of the present invention is disclosed, for example, in U.S. Pat. No. 5,249,391. Although micro-injection units are preferred, macro-injection units designed for use with injection holes that are ⅜ of an inch or greater in diameter and at least two inches in depth are also useful in carrying out injection for purposes of the present invention. It is stressed that the method described herein is not limited to micro- and macro-injection units, in that other injection technologies are also possible, including "gun" type injection units and later-developed injection technologies.

Injection units 14 each include a reservoir carrying a supply of solution 16 containing indolebutyric acid (IBA). A dilute solution comprising from 30 to 50 parts per million of IBA in distilled water is recommended, and a dilute solution comprising 40 parts per million of IBA in distilled water has been used in trials described below. IBA has long been associated with the commercial production of ornamental or agronomic plant species by promoting the generation of new roots on succulent vegetative cuttings. To applicant's knowledge, IBA has never been injected into or otherwise applied to trees for deflowering purposes. IBA is known to undergo fatty acid hydrolysis in treated cuttings whereby it is converted to indoleacetic acid (IAA), which is thought to provide the hormonal stimulus for tissue de-differentiation at the cut edge of the shoot to re-form cells into functional vascular tissue. Accordingly, the method of the present invention also encompasses injecting a solution containing IAA into the vascular system of tree 10.

EXAMPLE

Due to the unusually warm winter of 1998, sweet gum trees in the Micanopy, Fla. area began to produce staminate flowers in late November, despite the fact that sweet gum flower production does not ordinarily begin in this area until late January or early February. On Nov. 21, 1998, five sweet gum trees were selected for experimental treatment on a seven-acre tract near Micanopy. These trees ranged in diameter from twelve to eighteen inches at breast height (DBH). Each treated tree received TREE TECH® micro-injection units containing 5 mL of a 40 parts per million solution of IBA in distilled water at the rate of one micro-injection every six inches of trunk circumference near the base of the tree six to twelve inches above the ground line. Five additional trees were selected as untreated controls in this experiment. The experiment was terminated at the end of the third week of March, 1999.

Observations were conducted at weekly intervals over the next four months after injection with a consistent trend observed regarding the abscission of staminate flowers. At approximately two-week intervals throughout this trial period, populations of staminate flowers would develop to a height of about 1.25 to 1.5 inches and then develop a reddish off-color appearance which would rapidly turn brownish-black and the flower would be shed. At the same time, no pistillate flowers were observed and were assumed to have been either aborted or shed very early in the development process.

Staminate flowers were subtended by a cluster of young leaves which also were shed at the same time as the staminate flowers. In late February, 1999, it was observed that the staminate flowers were continuing to be shed at the same approximately two-week intervals, but the subtending foliage was no longer being shed. After the shedding of the initial group of staminate flowers, an additional population of staminate flower buds would develop and produce male floral structures until reaching the same approximate height at about two weeks time. At this same developmental stage, this second population of staminate flowers would rapidly become discolored and would be shed. Successive population waves of staminate flowers followed at approximately two-week intervals through the third week of March, 1999, when the finite population of staminate flower buds was consumed. In early March, 1999, vegetative buds which produced additional shoot growth and foliage began to be produced and by the end of the experiment, these were the only buds continuing to develop.

The staminate flowers of the five untreated control trees developed in normal fashion with yellowish-green flowers developing to an approximate height of 2 to 2.5 inches. These staminate flowers remained on the control trees for one month or more. The pistillate flower which was associated with each staminate flower was frequently pollinated and the developing fruit head was easily observed.

At the conclusion of the experiment, none of the five treated trees exhibited any developing fruit heads. With no further flower buds available this season, the treatment was concluded to be a successful method for shedding of staminate flowers and possible early abortion or suppression of pistillate flowers so that no fruit heads developed and ultimately no seed was produced.

What is claimed is:

1. A method of deflowering a sweet gum tree comprising the step of injecting a solution containing synthetic indolebutyric acid into vascular tissue of said tree, said step of injecting said solution being performed when male and female flowers of said sweet gum tree approach physiological maturity at or prior to fertilization.

2. The method of deflowering a sweet gum tree according to claim 1, wherein said solution is injected into said vascular tissue through a plurality of injection holes bored at spaced intervals about the circumference of the trunk of said tree.

3. The method of deflowering a sweet gum tree according to claim 2, wherein said plurality of injection holes are spaced approximately six inches apart about said circumference.

4. The method of deflowering a sweet gum tree according to claim 3, wherein said solution contains about 40 parts per million of indolebutyric acid in water, and five milliliters of said solution is injected through each of said plurality of injection holes.

5. The method of deflowering a sweet gum tree according to claim 1, wherein said solution contains from 30 to 50 parts per million of indolebutyric acid in water.

6. The method of deflowering a sweet gum tree according to claim 5, wherein said solution contains about 40 parts per million of indolebutyric acid in water.

* * * * *